United States Patent [19]

Morancais et al.

[11] Patent Number: 5,670,099
[45] Date of Patent: *Sep. 23, 1997

[54] PROCESS FOR PREPARING SUBMICRON PARTICLES IN THE PRESENCE OF LIPID VESICLES, AND CORRESPONDING COMPOSITIONS

[75] Inventors: Jean-Luc Morancais, Ozoir-la-Ferriere; Alain Lety, Lagny-sur-Marne; Guy Vanlerbergue, Villevaude, all of France

[73] Assignee: L'Oreal, France

[*] Notice: The term of this patent shall not extend beyond the expiration date of Pat. No. 5,425,993.

[21] Appl. No.: 315,869

[22] Filed: Sep. 30, 1994

Related U.S. Application Data

[62] Division of Ser. No. 971,971, filed as PCT/FR92/00569, Jun. 23, 1992, Pat. No. 5,425,993.

[30] Foreign Application Priority Data

Jun. 24, 1991 [FR] France .................. 91 07727

[51] Int. Cl.$^6$ .............. B01J 13/20; B01J 13/12; G03C 1/725
[52] U.S. Cl. .................. 264/4.3; 8/647; 8/649; 106/420; 106/498; 264/4.32; 428/402.2; 428/402.22; 428/402.24
[58] Field of Search ............. 264/4.1, 4.3, 4.32, 264/4.7; 427/2.23, 213.31; 428/402.2, 402.24, 402.22; 8/647, 649; 106/498, 420; 528/423; 525/909

[56] References Cited

U.S. PATENT DOCUMENTS

| | | | |
|---|---|---|---|
| 1,043,646 | 11/1912 | Turner | 423/604 |
| 4,208,183 | 6/1980 | Grollier et al. | 8/409 |
| 4,217,344 | 8/1980 | Vanlerberghe et al. | 428/402.2 |
| 4,485,045 | 11/1984 | Regen | 264/4.3 X |
| 4,772,471 | 9/1988 | Vanlerberghe et al. | 424/450 |
| 4,808,480 | 2/1989 | Regen | 428/402.2 |
| 4,830,857 | 5/1989 | Handjani et al. | 424/450 |
| 4,839,111 | 6/1989 | Huang | 264/4.6 |
| 5,104,736 | 4/1992 | Wallach | 428/402.2 |
| 5,123,414 | 6/1992 | Unger | 264/4.3 X |
| 5,147,723 | 9/1992 | Wallach | 428/402.2 |
| 5,234,767 | 8/1993 | Wallach | 428/402.2 |
| 5,252,706 | 10/1993 | Kitaguchi et al. | 530/329 |
| 5,425,993 | 6/1995 | Morancais et al. | 428/402.24 |

FOREIGN PATENT DOCUMENTS

| | | | |
|---|---|---|---|
| 0227141 | 7/1987 | European Pat. Off. | 430/617 |
| A1344040 | 11/1989 | European Pat. Off. | |
| B1344040 | 11/1989 | European Pat. Off. | |
| 210353 | 6/1984 | Germany | |
| 1136915 | 6/1986 | Japan | 423/604 |

OTHER PUBLICATIONS

World Patents Index Latest, Derwent Publications Ltd., AN 90-166618 (22) & JP, A, 1 105 826, Apr. 1990.

World Patents Index Latest, Derwent Publications Ltd., AN 90-166619 (22) & JP, A, 2 105 827, Apr. 1990.

Tricot et al, "Colloidal catalyst–coated semiconductors in surfactant vesicles: in situ generation of rh–coated cds particles in dihexadecylphosphate vesicles and their utilization for photosensitized charge separation and hydrogen generation", J. Am. Chem. Soc., vol. 106, 1984 pp. 7359–7366.

Torchilin et al, "Polymerization of liposome–encapsulated hydrophilic monomers", Markomol. Chem., Rapid Commun., vol. 8, 1987, pp. 457–460.

*Primary Examiner*—Richard D. Lovering
*Attorney, Agent, or Firm*—Cushman Darby & Cushman IP Group of Pillsbury Madison & Sutro

[57] ABSTRACT

Process for obtaining submicronic particles, for example, pigments in the presence of lipidic vesicles having a lamellar structure, starting with at least one precursor of said particles involves preparing a dispersion of vesicles starting with at least one lipid capable of forming the walls of the vesicles and an aqueous phase E intended to be encapsulated in the said vesicles, and optionally an aqueous phase D, intended to form a dispersion medium of the said vesicles, at least one precursor of the said vesicles being dissolved in phase E and/or D, before and/or during and/or after the preparation of the vesicular phase, at least one agent capable of transforming the said precursor(s) into sought after particles being reacted with it (them) after introduction into the preparation medium.

13 Claims, No Drawings

PROCESS FOR PREPARING SUBMICRON PARTICLES IN THE PRESENCE OF LIPID VESICLES, AND CORRESPONDING COMPOSITIONS

This is a division of application Ser. No. 07/971,971, filed Feb. 19, 1993, now U.S. Pat. No. 5,425,993, filed as PCT/FR92/00569, Jun. 23, 1992.

The present invention concerns a process for the preparation of submicronic particles of pigments or polymers in combination with lipidic vesicles having a lamellar structure, the walls of which are leaves constituted of at least one lipidic bi-layer, as well as compositions obtained by this process.

Such particles are quite desired principally in the preparation of pigments, semi-conductors, catalysts, ceramics or photographic emulsions. In the field of pigments, the reduction of the size of the particles permits, principally, to improve the stability of pigment dispersions vis-a-vis a sedimentation phenomenon and an increase in the covering power of the said pigments.

One of the processes presently employed for the preparation of submicronic particles consists in encapsulating the precursor of these particles in the lipidic vesicles, then eliminating, generally by gel filtration, the excess precursor which is found at the exterior of the said vesicles, and then forming these particles in situ.

It is thus that S. Mann and J. P. Hammington have described, in "Journal of Colloid and Interface Science", Vol. 122, No. 2, April, 1988, pages 326–335, the preparation of metallic particles of iron oxide having a size ranging from 5 to 12 nm. To this effect, aqueous solutions of Fe (III) and/or Fe (II) are encapsulated in vesicles formed from phosphatidylcholine; the iron salts exterior to the vesicles are eliminated by chromatography on an ion exchange column. The pigments are precipitated at the interior of the vesicles by the addition of soda or ammonia. The vesicle solutions trapping the precipitates can be stored in the dark at 4° C., for a period of time ranging from 8 to 10 days.

In "Makromol. Chem., Rapid Commun", 8, 457–460, (1987), V. P. Torchilin et al have described the preparation of polymeric particles having a size ranging from 500 to 700 nm in a dispersion of ionic lipidic vesicles in an aqueous monomer solution. The monomers exterior to the vesicles are eliminated by gel exclusion chromatography. Finally, the polymerization is effected in situ at the interior of the liposomes by ultraviolet irradiation.

In Japanese patent applications published under Nos. 90 105827 and 90 05826, there is described the preparation of polymeric particles by dispersion of lipids in a solution of water soluble monomers. The monomer is found encapsulated in the vesicles; in the first patent application the excess of monomer is eliminated by known procedures, such as gel filtration or ion exchange resin filtration; in the second patent application, the monomer excess is rendered inactive by the addition, to the dispersion of vesicles, of a polymerization inhibitor. Polymerization is then effected in situ by irradiation.

There has also been described (Rafalloff et al. J. Phys. Chem. 1985, 89, 533–537) the preparation of submicronic particles of cadmium sulfate. An aqueous solution of a cadmium/EDTA complex (EDTA=ethylenediamine tetraacetic acid) is encapsulated at the interior of vesicles formed by dimethyl dioctadecylammonium bromide (or chloride). The excess of the complex, that is to say that which is found at the exterior of the vesicles, is not eliminated. However, the lipids forming the vesicles and the complexes are selected so that there is sorption of the complex at the internal and external surface of the vesicular membranes. Precipitation of the cadmium sulfate is obtained by bubbling $H_2S$.

In a similar manner, Y. M. Tricot and J. M. Fendler (J. Phys. Chem., 1986, 90, 3369–3374) have described a process following which the sorption of cadmium at the interior and at the exterior of the surface of vesicular membranes is assured by encapsulating cadmium chloride in the vesicles formed from dihexadecylphosphate. There also, given the sorption of the cadmium ion, it is not necessary to eliminate excess aqueous solution containing these ions at the exterior of the vesicles. The precipitation of the cadmium sulfide is also obtained by bubbling $H_2S$.

It is then noted that the prior art procedures such as those described above, require, or indeed that there is effected a separation between the vesicles and the exterior medium before the formation of pigments or polymers, or indeed that there is sorption of the precursor (of pigments or polymers) on the vesicles.

The present invention has for an object the simplification of the procedures for the preparation of submicronic particles of the pigment or polymer type, in combination with lipidic vesicles.

It has now been discovered, in a surprising manner, that it is possible, with the view of obtaining pigments or polymers in the form of submicronic particles, to carry out chemical reactions and, principally, polymerizations and precipitations, in a microstructured medium, which occur not only at the interior of the vesicles, but also at the exterior thereof. This permits to avoid the above noted exigencies, which represents a very significant advantage with respect to prior art processes.

According to the present invention, there is proposed a process involving the solubilization of precursors of polymers or pigments, in an internal medium and/or in the dispersion medium of the vesicles, and the addition of agents permitting the transformation of the precursors into the expected pigments or polymers.

The present invention has then for an object a process for the preparation of submicronic particles in the presence of lipidic vesicles, starting with at least one precursor of said particles, in which a dispersion of vesicles is prepared starting with at least one lipid capable of forming vesicles and an aqueous phase E intended to be encapsulated in the said vesicles, and optionally, an aqueous phase D intended to form a dispersion medium for the said vesicles, characterized by the fact that at least one precursor of the said particles is dissolved in the phase E and/or D, before and/or during and/or after the preparation of the vesicular phase and at least one agent capable of transforming the-said precursor (s) into the sought after particles is introduced so as to react with it (or them) after its (or their) introduction into the preparation medium.

The precursors dissolved in water can be introduced at whatever step of the preparation of the vesicular dispersions. It results from it that the submicronic particles are present either essentially at the interior of the vesicles, or essentially at the exterior of the vesicles, or again in the interior as well as the exterior thereof.

Thus the process which is the object of the invention is applicable to any vesicular dispersion, regardless of its process of preparation.

A disclosure of various methods of preparation can be found in "Les liposomes en biologie cellulaire etpharmacologie", Editions INSERM/John Libbey Eurotext, 1987, pages 6–18.

In accordance with a first embodiment of the invention, there is employed at least one precursor capable of precipitating into submicronic particles under the action of at least one precipitation agent; in accordance with a second embodiment of the invention, there is employed, as a precursor, at least one polymerizable monomer, which is reacted with at least one polymerization agent.

Preferably, the transformation of the precursor(s) is effected after the formation of the vesicles.

The lipid(s) are selected from among nonionic amphiphilic lipids, ionic amphiphilic lipids, and mixtures of nonionic and ionic lipids.

Among the useful nonionic amphiphilic lipids, mention can be made of the following nonionic amphiphilic lipids:

(1) linear or branched polyglycerol derivatives having the formula $$R^0O \!+\! C_3H_5(OH)O \!\!\mid_{\overline{n}}\!\! H \qquad (I)$$

wherein

—$C_3H_5(OH)O$— is represented by the following structures taken in admixture or separately:

—$CH_2CHOHCH_2O$—, —$CH_2$—$\underset{\underset{CH_2OH}{|}}{CH}$O— and —$\underset{\underset{CH_2OH}{|}}{CH}$—$CH_2O$—;

$\overline{n}$ is a statistical average value ranging from 1 to 6;

$R^0$ represents:

(a) a linear or branched, saturated or unsaturated aliphatic chain containing from 12 to 30 carbon atoms; or hydrocarbon radicals of lanolin alcohol; or the residues of long chain α-diols;

(b) the residue $R^1CO$, wherein $R^1$ is a linear or branched aliphatic radical containing 11–29 carbon atoms;

(c) a residue $R^2\!-\!\!(OC_2H_3(R_3)\!)_{\overline{r}}$ wherein $R^2$ has the meaning (a) or (b) given for $R^0$ and $OC_2H_3(R^3)$ is represented by the following structures, taken in admixture or separately:

—$\underset{\underset{R^3}{|}}{OCH}$—$CH_2$— and —O—$CH_2$—$\underset{\underset{R^3}{|}}{CH}$—, wherein $R^3$ has the meaning (a) given for $R^0$;

(2) linear or branched polyglycerol ethers having two fatty chains;

(3) polyoxyethylenated fatty alcohols and polyoxyethylenated sterols and phytosterols;

(4) polyol ethers;

(5) polyol esters, oxyethylenated or not;

(6) glycolipids of natural or synthetic origin and principally the ethers and esters of glucose;

(7) hydroxyamides having the formula (II):

$$\underset{\underset{R^5-CONH}{|}}{R^4-CHOH-CH-COA} \qquad (II)$$

wherein $R^4$ represents a $C_7$–$C_{21}$ alkyl or alkenyl radical;

$R^5$ represents a saturated or unsaturated $C_7$–$C_{31}$ hydrocarbon radical;

COA represents a group selected from the following two groups, a $$\underset{\underset{R^6}{|}}{CON-B}$$

residue, wherein B is an alkyl radical derived from primary or secondary, mono or polyhydroxylated amines and R6 represents hydrogen or methyl, ethyl or hydroxyethyl; and a —COOZ residue wherein Z represents the residue of a $C_3$–$C_7$ polyol;

(8) glycerol derivatives described in PCT patent application No. 92/08685 and having the formula:

$$\underset{\underset{OH}{|}}{CH_2}-\underset{\underset{OH}{|}}{CH}-CH_2-O-\left[CH_2-\underset{\underset{R^7}{|}}{CH}-O\right]_m-H \qquad (III)$$

wherein $R^7$ represents linear $C_{14}$–$C_{18}$ alkyl or a —$CH_2A$ group wherein A is $OR_{14}$, $R_{14}$ represents a $C_{10}$–$C_{18}$ linear alkyl and, preferably $C_{16}$, and m has a statistical average value greater than 1 and at most equal to 3 and, besides, when $R^7$ is equal to —$CH_2A$, m can also represent an actual value (non-statistical) equal to 2;

(9) glucose esters having the formula (IV)

[structure of glucose ester with $OCR^8$ group]

wherein $R^8$ represents a linear, saturated or unsaturated hydrocarbon chain containing from 9 to 17 carbon atoms, these esters being described in European patent application No. 485 251.

Among the useful ionic amphiphilic lipids, mention can be made of:

natural phospholipids such as egg or soy lecithin and sphingomyelin;

synthetic phospholipids, such as dipalmitoylphosphatidylcholine or hydrogenated lecithin; and anionic compounds, such as dialkylphosphate acids or their salts such as, for example, dicetylphosphate;

quaternary ammonium cationic derivative compounds having the following formula (V)

$$\underset{R_{11}}{\overset{R_9}{\diagdown}}\!\!\overset{+}{N}\!\!\underset{R_{12}}{\overset{R_{10}}{\diagup}} \quad X^- \qquad (V)$$

wherein $R_9$ and $R_{10}$, each independently, represent $C_{12}$–$C_{20}$ alkyl; and $R_{11}$ and $R_{12}$, each independently, represent $C_1$–$C_4$ alkyl;

polymerizable lipids, such as those described by Ringsdorf and others in "Angewandte Chemie", Vol. 27, No. 1, January 1988, pages 129 and 137.

Besides, there can be combined with the lipids, additives selected from

. long chain alcohols and diols, sterols, for example, cholesterol, long chain amines and their quaternary ammonium derivatives;

dihydroxyalkyl amines, polyoxyethylenated fatty amines;

esters of long chain amino alcohols; and their salts and quaternary ammonium derivatives;

phosphoric esters of fatty alcohols;

alkyl sulfates, for example, sodium cetyl sulfate; and certain polymers, such as polypeptides and proteins.

Also, there can be combined with the lipidic phase of the vesicles, at least one lipoprotide, free of sulfhydryl function, selected from among the mono- or polyacyl derivatives of amino acids or polypeptides, in which the acyl residue $R_{13}$—CO has a $R_{13}$ hydrocarbon chain containing 13–19 carbon atoms, at least one of the functions which link the polypeptidic chain or the amino acid residue to the lipophilic chain being an amide function, the carboxylic functions of the polypeptidic chain or the amino acid residue being able to be partially or totally neutralized by one or more alkaline cations, an ammonium ion or a substituted ammonium derived from an amine, the said lipoprotide(s) being present in an amount ranging from 1 to 15 weight percent based on the total weight of the lipidic phase, and/or at least one cholesterol sulfate having an ammonium, alkali or alkaline earth cation, in an amount ranging from 1 to 50 weight percent based on the weight of the said lipidic phase.

Finally, there can be combined with the lipidic phase of nonionic lipids at least one cholesterol phosphate in the form of a free acid or neutralized by an ammonium, alkali or alkaline earth cation, in an amount ranging from 1 to 40 weight percent relative to the total weight of the said lipidic phase.

As the aqueous E or D phase, water, or a mixture of water and at least one water-miscible solvent advantageously selected from among $C_1$–$C_7$ alcohols and $C_1$–$C_5$ alkyl polyols can be employed.

According to the invention, there is advantageously prepared submicronic particles constituted by pigments or polymers, by employing precipitation or polymerization agents compatible with the vesicles on the chemical or physicochemical level and selected principally from among oxidizing agents, free radical initiators, enzymes, radiations, acids and bases, the precipitation of the pigments being able to result principally from a hydrolysis reaction in an organic medium or, in an aqueous medium, of a reaction starting with chelates, of a decomposition or double decomposition reaction, of a redox reaction, of a chemical reaction between two organic precursors soluble in the reaction medium and leading to an insoluble species in this medium, or of the action of a poor solvent on the precursor of the considered pigment.

Thus, the process of the invention is applicable to the preparation of mineral pigments according to the following reactions:

hydrolysis reactions in an organic medium (alcohols) such as, for example:

metallic alkoxides→$TiO_2$, $BaTiO_3$, $ZnO$;

hydrolysis reactions in an aqueous medium, for example:

metallic salts→$Cr(OH)_3$, $Al(OH)_3$, $TiO_2$, $Fe_2(SO_4)_3$, $Ag_2O$;

reactions starting with chelates, as, for example:

MS with M = Pb, Cu, Zn and $1 \leq n \leq 4$, decomposition reactions, as for example:

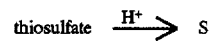

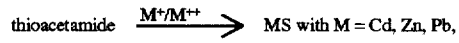

redox reactions, as for example:

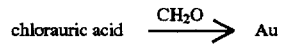

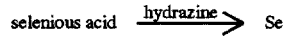

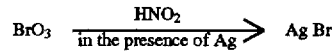

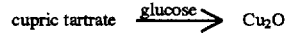

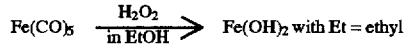

double decomposition reactions as, for example:

$NH_4Cl + AgNO_3 \rightarrow AgCl + NH_4NO_3$ $KIO_3 + Pb(NO_3)_2 \rightarrow Pb(IO_3)_2$ $KIO_3 + La(NO_3)_3 \rightarrow La(IO_3)_3$ Ferric perchlorate+phosphoric acid→$FePO_4$ precipitation by a poor solvent.

In a preferred embodiment, submicronic particles of pigments are obtained by oxidation or by oxidizing or enzymatic polymerization of at least one indolic compound and/or at least one indolinic compound.

The indolic compound is selected principally from among those having the formula:

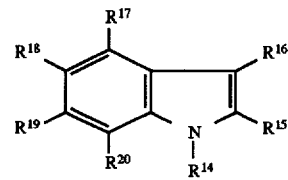

(VI)

wherein $R^{14}$ and $R^{16}$, each independently, represent hydrogen or $C_1$–$C_4$ alkyl;

$R^{15}$ represents hydrogen, $C_1$–$C_4$ alkyl, carboxyl or $C_1$–$C_4$ alkoxy carbonyl;

$R_{17}$ and $R^{20}$, each independently, represent hydrogen, hydroxy, $C_1$–$C_4$ alkyl, amino, $C_1$–$C_4$ alkoxy, ($C_1$–$C_4$ alkoxy)oxy, ($C_2$–$C_4$ acyl) amino;

$R^{18}$ represents hydrogen, hydroxy, $C_1$–$C_4$ alkoxy, $C_1$–$C_4$ alkyl, halogen, amino, ($C_2$–$C_4$)acyloxy, ($C_2$–$C_4$ acyl) amino, trimethylsilyloxy;

$R^{19}$ represents hydrogen, hydroxy, $C_1$–$C_4$ alkoxy, amino, ($C_2$–$C_4$ acyl)oxy, ($C_2$–$C_4$ acyl) amino, trimethylsilyloxy, ($C_2$–$C_4$ hydroxyalkyl) amino;

$R^{18}$ and $R^{19}$ can also form, together with the carbon atoms to which they are attached, a methylenedioxy ring, optionally substituted by a $C_1$–$C_4$ alkyl group or a $C_1$–$C_4$ alkoxy group, or even a carbonyldioxy ring;

with the proviso that at least one of $R^{17}$ to $R^{20}$ radicals represents an OZ or $NHR^{21}$ group with at most one of the $R^{17}$ to $R^{20}$ groups representing $NHR^{21}$; and at most two of the $R^{17}$ to $R^{20}$ groups representing OZ and, in the circumstance where Z represents hydrogen the two OH groups are in positions 5 and 6; and at least one of the $R^{17}$ to $R^{20}$ radicals represent hydrogen, and in the circumstance where only one of these radicals represents hydrogen, a single radical among $R^{17}$ to $R^{20}$ then represents $NHR^{21}$ or OZ, the other radicals representing a $C_1-C_4$ alkyl;

$R^{21}$ represents hydrogen, $C_2-C_4$ acyl, $C_2-C_4$ hydroxyalkyl, and

Z represents hydrogen, $C_2-C_{14}$ acyl $C_1-C_4$ alkyl or trimethylsilyl;

and their alkali metal, alkaline earth metal, ammonium or amine salts as well as the corresponding hydrochlorides, hydrobromides, sulfates and methanesulfonates.

These indolic compounds are preferably selected from the group consisting of 4-hydroxyindole,
5-hydroxyindole,
6-hydroxyindole,
7-hydroxyindole,
4-hydroxy-5-methoxyindole,
4-hydroxy-5-ethoxyindole,
2-carboxy-5-hydroxyindole,
5-hydroxy-6-methoxyindole,
6-hydroxy-7-methoxyindole,
5-methoxy-6-hydroxyindole,
5,6-dihydroxyindole,
N-methyl-5,6-dihydroxyindole,
2-methyl-5,6-dihydroxyindole,
3-methyl-5,6-dihydroxyindole,
2,3-dimethyl-5,6-dihydroxyindole,
2-carboxyl-5,6-dihydroxyindole,
4-hydroxy-5-methylindole,
2-carboxyl-6-hydroxyindole,
6-hydroxy-N-methylindole,
2-ethoxycarbonyl-5,6-dihydroxyindole,
4-hydroxy-7-methoxy-2,3-dimethylindole,
4-hydroxy-5-ethoxy-N-methylindole,
6-hydroxy-5-methoxy-2-methylindole,
6-hydroxy-5-methoxy-2,3-dimethylindole,
6-hydroxy-2-ethoxycarbonylindole,
7-hydroxy-3-methylindole,
5-hydroxy-6-methoxy-2,3-dimethylindole,
5-hydroxy-3-methylindole,
5-acetoxy-6-hydroxyindole,
5-hydroxy-2-ethoxycarbonylindole,
6-hydroxy-2-carboxyl-5-methylindole,
6-hydroxy-2-ethoxycarbonyl-5-methoxyindole,
6-N-β-hydroxyethylaminoindole,
4-aminoindole,
5-aminoindole,
6-aminoindole,
7-aminoindole,
N-methyl-6-β-hydroxyethylaminoindole,
6-amino-2,3-dimethylindole,
6-amino-2,3,4,5-tetramethylindole,
6-amino-2,3,4-trimethylindole,
6-amino-2,3,5-trimethylindole,
6-amino-2,3,6-trimethylindole,
5,6-diacetoxyindole,
5-methoxy-6-acetoxyindole and
5,6-dimethylindole, and
the addition salts of these compounds.

5,6-dihydroxyindole and 6-hydroxyindole are particularly preferred.

The indolinic compound is selected preferably from among those having the formula:

(VII)

wherein $R^{22}$ and $R^{24}$, each independently, represent hydrogen or $C_1-C_4$ alkyl, $R^{23}$ represents hydrogen, $C_1-C_4$ alkyl, carboxyl or $C_1-C_4$ alkoxycarbonyl;

$R^{25}$ represents hydrogen, $C_1-C_4$ alkyl, hydroxyl, $C_1-C_4$ alkoxy, amino, $C_1-C_{10}$ alkylamino or halogen;

$R^{26}$ represents hydrogen, hydroxy, $C_1-C_4$ alkoxy or amino;

with the proviso that at least one of $R^{25}$ or $R^{26}$ represents hydroxyl, alkoxy or amino; and with the proviso that when $R^{26}$ represents amino, $R^{25}$ does not represent alkylamino;

$R^{25}$ and $R^{26}$ can also form a $C_1-C_2$ alkylenedioxy ring when they are in positions 5 and 6; as well as their corresponding salts.

Among the compounds of formula (VII) the preferred compounds employed in accordance with the invention are selected from the group consisting of:

5,6-dihydroxyindoline,
6-hydroxyindoline,
5,6-methylenedioxyindoline,
7-methoxy-6-hydroxyindoline,
6,7-dihydroxyindoline,
5-hydroxy-4-methoxyindoline,
4,5-dihydroxyindoline,
5-methoxy-6-hydroxyindoline,
4-hydroxy-5-methoxyindoline,
5-hydroxy-6-methoxyindoline,
4,7-dihydroxyindoline,
6-aminoindoline,
N-ethyl-4-hydroxyindoline,
1-ethyl-6-aminoindoline,
5,6-diaminoindoline,
1-methyl-6-aminoindoline,
2-methyl-6-aminoindoline,
3-methyl-6-aminoindoline,
2-methyl-5,6-diaminoindoline,
5-chloro-7-aminoindoline, 3-methyl-5,7-diaminoindoline, 5,7-diaminoindoline, 2-methyl-5,7-diaminoindoline, 7-aminoindoline, 2-methyl-7-aminoindoline, 4-aminoindoline, 4-amino-6-chloroindoline, 4-amino-6-iodoindoline, 4-amino-5-bromoindoline, 4-amino-5-hydroxyindoline, 4-amino-7-hydroxyindoline, 4-amino-5-methoxyindoline, 4-amino-7-methoxyindoline, 5-aminoindoline, 2,3-dimethyl-5-aminoindoline, 1-methyl-5-aminoindoline, 2-methyl-5-aminoindoline, 5-N-(1-methylhexyl) aminoindoline, 5,6-dimethoxyindoline and 5,6-dihydroxy-2-carboxy indoline.

In the compounds of formula VII, the $C_1$–$C_4$ alkyl radicals preferably represent methyl, ethyl, propyl, isopropyl, butyl and isobutyl; the $C_1$–$C_{10}$ alkyl radicals preferably represent, methyl, ethyl, propyl, isopropyl, butyl, isobutyl, 1-methylhexyl, 1-methylheptyl, 1-methyloctyl; the alkoxy radicals preferably represent methoxy, ethoxy, propoxy and butoxy; halogen preferably represents bromine, chlorine or iodine.

The salts of the compounds of formula VII are, in particular, the hydrochlorides, hydrobromides, sulfates, methanesulfonates or the salts of alkali metals, alkaline earth metals, ammonium or amines. The hydrobromides of the compounds of formula VII are particularly preferred.

The oxidation of the indolic compound of formula VI or the indolinic compound of formula VII can be carried out in an aqueous or solvent-water medium, in air, in the presence or not of an alkaline agent and/or a metallic oxidation catalyst. A preferred metallic oxidation catalyst is constituted by the cupric ion.

The reaction medium is, preferably, constituted by water and can, the case being, be constituted by a mixture of water and at least one solvent selected so as to rapidly dissolve the indolic compound of formula VI or the indolinic compound of formula VII. Among these solvents mention can be made of, as examples, $C_1$–$C_7$ lower alcohols, such as ethyl alcohol, propyl or isopropyl alcohol, tert. butyl alcohol, alkyleneglycols such as ethyleneglycol, propyleneglycol, alkylethers of alkyleneglycols such as the mono-methyl, monoethyl and monobutyl ethers of ethyleneglycol, the monomethylethers of propyleneglycol and dipropyleneglycol, and methyl lactate.

Oxidation can also be effected by employing hydrogen peroxide in the presence of an alkaline agent, such as, preferably, ammonia, or in the presence of an iodide ion, the iodide being, preferably, the iodide of an alkali metal, an alkaline earth metal or ammonium.

Oxidation can also be effected by using periodic acid and its water-soluble salts and derivatives; permanganates and dichromates, such as sodium or potassium, sodium hypochlorite, potassium ferricyanide, ammonium persulfate, silver oxide, lead oxide, ferric chloride, sodium nitrite, rare earth salts and principally those of cerium and organic oxidants selected from the ortho and parabenzoquinones, the ortho- and parabenzoquinone mono- or diimines, 1,2- and 1,4-naphthoquinones, 1,2- and 1,4-naphthoquinone mono- or diimines. The preferred periodic acid salt is sodium periodate.

It is possible to activate the oxidizing agents by a pH modifier. For example, during the use of the iodide/hydrogen peroxide system there can be employed, preferably, an alkaline medium which permits to activate the reaction.

Also envisaged is an enzymatic oxidation.

The pigments according to the invention can also be obtained by the oxidizing or enzymatic polymerization of precursors such as L-tyrosine, L-dopa, catechol and their derivatives.

According to the invention, particles of acrylamide and bis-acrylamide polymers can also be prepared.

There can also be prepared particles of polymers by precipitation of the polymers in solution under the effect of a pH change.

In accordance with a particular embodiment of the present invention, a lamellar phase is prepared, by dissolving the lipid(s) in a solvent before forming the wall of the vesicles, evaporating the solvent under reduced pressure, then admixing the lipidic combination thus formed with the aqueous phase E, homogenizing and heating the mixture to a temperature of 10°–150° C., preferably 40°–80° C., for 0.25 hours and returning the temperature to ambient temperature. The cycle: homogenization-heating-return to ambient temperature is repeated at least once. There is advantageously employed, as solvent, dichloromethane, chloroform, ethyl acetate, butyl acetate, ethyl formate, hexane, cyclohexane, toluene, petroleum ether, methanol, ethanol, propanol, methyl ether, ethyl ether and mixtures of at least two of them.

In accordance with a particular method of operation of the present invention, a lamellar phase is advantageously prepared in which the lipid concentration lies between 10 and 90 weight percent, preferably between 20 and 80 weight percent; the vesicular phase is prepared by homogenizing the mixture of the lamellar phase and phase D by at least one mechanical means of the shaking type and/or ultrasound type; the vesicular phase is prepared at a temperature between 10° and 150° C., preferably between 40° and 80° C.; a vesicular phase is prepared in which the lipid concentration lies between 1 and 90 weight percent, preferably between 5 and 20 weight percent; and the vesicles have a size between 20 and 3,000 nm, preferably between 20 and 500 nm.

A medium is advantageously obtained in which are dispersed lipidic vesicles and submicronic particles, the said particles being contained in the said vesicles and/or independent of them, the volume of said vesicles and, the case being, of particles independent of it, representing 5 to 90 percent, preferably 10 to 70% of the volume of the medium.

The invention-also has for an object a composition obtained by the process defined above.

According to a particular embodiment, the composition according to the invention comprises, in an aqueous medium, from 0.1 to 20% and preferably, from 0.1 to 5 percent by weight of pigment particles having a size between 20 and 500 nm, the percentages being given with respect to the total weight of the composition.

To better understand the object of the invention, there are now described, as purely illustrative and non-limiting examples, several methods of operation. In these examples, the indicated percentages are given by weight, except when indicated to the contrary.

EXAMPLE 1

First stage:

There is employed a lipidic phase formulated as follows:
Nonionic amphiphilic lipid of formula VIII:

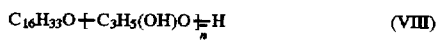

wherein

—$C_3H_5(OH)O$— is represented by the following structures, taken in admixture or separately:

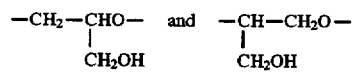

and $\bar{n}$ has

| a statistical average value equal to 3 | 1.43 g |
| --- | --- |
| Cholesterol | 1.43 g |
| Sodium dihexadecyl phosphate | 0.14 g |

These said components are introduced into a 50 ml round bottom flask and are dissolved in 10 ml of dichloromethane. Finally, the solvent is evaporated at 40° C. under reduced pressure, in successive stages ranging from ambient pressure up to about 500 Pa, using a rotary evaporator.

Second stage:

The lipidic film formed at the end of the first stage is removed and placed in a 60 ml flask. 3.00 g of water are added to the lipids. The resulting mixture is submitted to the following cycle, which is repeated 4 times: homogenization using a spatula—oven heating at 75° C. for 1 hour—returning to ambient temperature by spontaneous cooling in air.

Third stage:

To the lamellar phase at the end of the second stage, there are added 22.40 g of a solution containing 1.21% of 5,6-dihydroxyindole and 0.51% of potassium iodide in water. The mixture thus obtained is stirred by shaking, for 15 minutes, at ambient temperature.

Fourth stage:

To the dispersion obtained at the end of the third stage, there is added, with mild stirring, 0.50 g of a 0.1M solution of sodium hydroxide in water. The pH of the dispersion is equal to 7.47.

Fifth stage:

To the dispersion obtained at the end of the fourth stage, 1.40 g of a solution of hydrogen peroxide at 22.4 volumes in water are added. The mixture, brought to a temperature of 30° C., is treated for 8 minutes with an ultrasound homogenizer. The resulting vesicle dispersion is then left at rest at ambient temperature.

The weight composition of the preparation thus realized is as follows:

| Nonionic lipid of formula VIII | 4.73% |
| --- | --- |
| Cholesterol | 4.73% |
| Sodium dihexadecylphosphate | 0.46% |
| Polymerized 5,6-dihydroxyindole | 0.90% |
| Aqueous excipient, sufficient amount for | 100% |

The volume fraction of the particles dispersed in this preparation (vesicles and pigments based on polymerized 5,6-dihydroxyindole) is equal to 38%, after a day of storage at ambient temperature.

The average size of the dispersed particles (vesicles and pigments) measured after 7 days of storage at ambient temperature is equal to 281±3 nm; and the average size of the pigments, measured after 14 days of storage at ambient temperature is equal to 202±7 nm.

EXAMPLE 2

First stage:

A lipidic phase formulated as follows is employed:

| Nonionic lipid of formula VIII | 0.71 g |
| --- | --- |
| Cholesterol | 0.71 g |
| Sodium dihexadecyl phosphate | 0.08 g |

The procedures set forth in the first stage of Example 1 are followed.

Second stage:

The procedures given for the second stage of Example 1 are followed except that 1.50 g of water are added.

Third stage:

To the lamellar phase obtained at the end of the second stage there are added 25.30 g of a solution containing 1.13% of 5,6-dihydroxyindole and 0.48% of potassium iodide in water. The mixture thus obtained is stirred by shaking for 15 minutes at ambient temperature.

Fourth stage:

To the dispersion obtained at the end of the third stage, there is added, with mild stirring, 0.70 g of a 0.1M solution of sodium hydroxide in water. The pH of the dispersion is equal to 7.50.

Fifth stage:

The procedures of the fifth stage of Example 1 are followed except that 1.50 g of a hydrogen peroxide solution at 22.4 volumes in water are employed.

The weight composition of the preparation thus produced is the following:

| Nonionic lipid of formula VIII | 2.32% |
| --- | --- |
| Cholesterol | 2.32% |
| Sodium dihexadecylphosphate | 0.26% |
| Polymerized 5,6-dihydroxyindole | 0.94% |
| Aqueous excipient, sufficient amount for | 100% |

The volume fraction of the particles dispersed in this preparation (vesicles and pigments based on polymerized 5,6-dihydroxyindole) is equal to 29% after a day of storage at ambient temperature.

The average size of the dispersed particles (vesicles and pigments) measured after a day of storage at ambient temperature is equal to 326±8 nm; and the average size of the pigments, measured after a day of storage at ambient temperature is equal to 188±3 nm.

EXAMPLE 3

First stage:

A lipidic phase formulated as follows is employed:

| Nonionic lipid of formula VIII | 1.16 g |
| --- | --- |
| Cholesterol | 1.16 g |
| Sodium dihexadecylphosphate | 0.12 g |

The procedures given in the first stage in Example 1 are followed.

13

Second stage:

The procedures given in the second stage in Example 1 are followed except that 2.45 g of water are employed.

Third stage:

To the lamellar phase obtained at the end of the second stage, there are added 19.21 g of a solution containing 1.00% of 5,6-dihydroxyindole in water. The mixture thus obtained is stirred by shaking for 15 minutes at ambient temperature.

Fourth stage:

To the dispersion obtained at the end of the third stage, there is added 0.54 g of a solution of hydrogen peroxide at 17.5 volumes in water. The mixture thus obtained is treated for 8 minutes with an ultrasound homogenizer.

Fifth stage:

The vesicle dispersion obtained at the end of the fourth stage is maintained under mild mechanical stirring and brought to a temperature of 80° C. for 4 hours.

The weight composition of the preparation thus produced is the following:

| Nonionic lipid of formula VIII | 4.64% |
|---|---|
| Cholesterol | 4.64% |
| Sodium dihexadecylphosphate | 0.49% |
| Polymerized 5,6-dihydroxyindole | 0.78% |
| Aqueous excipient, sufficient amount for | 100% |

The volume fraction of particles dispersed in this preparation (vesicles and pigments based on polymerized 5,6-dihydroxyindole) is equal to 49% after one day of storage at ambient temperature.

The average size of the dispersed particles (vesicles and pigments), measured after one day of storage at ambient temperature, is equal to 232±6 nm; and the average size of the pigments, measured after one day of storage at ambient temperature is equal to 183±2 nm.

EXAMPLE 4

First stage:

A lipidic phase formulated as follows is employed:

| Nonionic lipid of formula VIII | 1.25 g |
|---|---|
| 2-doicosanoylamino-1,3-octadecanediol | 0.26 g |
| Cholesterol | 0.99 g |
| Sodium dihexadecylphosphate | 0.13 g |

The procedures given for the first stage in Example 1 are followed.

Second stage:

The procedures given for the second stage in Example 1 are followed except that 2.64 g of water are employed.

Third stage:

The procedures given for the third stage in Example 1 are followed, except that there are added 19.30 g of a solution containing 1.00% of 5,6-dihydroxyindole and 0.42% of potassium iodide in water.

Fourth stage:

To the dispersion obtained at the end of the third stage, there is added, under mild stirring, 0.20 g of a 0.1M solution of sodium hydroxide in water. The pH of the dispersion is equal to 7.58.

Fifth stage:

The procedures given for the fifth stage of Example 1 are followed.

14

The weight composition of the preparation thus produced is the following:

| Nonionic lipid of formula VIII | 4.83% |
|---|---|
| 2-doicosanoylamino-1,3-octadecanediol | 1.02% |
| Cholesterol | 3.81% |
| Sodium dihexadecylphosphate | 0.51% |
| Polymerized 5,6-dihydroxyindole | 0.75% |
| Aqueous excipient, sufficient amount for | 100% |

The volume fraction of the particles dispersed in this preparation (vesicles and pigments based on polymerized 5,6-dihydroxyindole) is equal to 35% after 12 days of storage at ambient temperature.

The average size of the dispersed particles (vesicles and pigments), measured after 12 days of storage at ambient temperature, is equal to 243±4 nm; and the average size of the pigments, measured after 21 days of storage at ambient temperature, is equal to 192±3 nm.

EXAMPLE 5

First stage:

A lipidic phase formulated as follows is employed:
Nonionic amphiphilic lipid having the formula:

$$C_{12}H_{25}[OC_2H_3(R')\!-\!\!+\!\!O\!-\!\!+\!C_3H_5(OH)O\,]_{\overline{n}}H \qquad (IX)$$

wherein

—$C_3H_5(OH)O$— is constituted by a mixture of the radicals, $$-CH_2-CHO- \text{ and } -CH-CH_2O-$$
$$\phantom{xxxxx}|\phantom{xxxxxxxxxxxx}|$$
$$\phantom{xxxx}CH_2OH\phantom{xxxxx}CH_2OH$$

and —$OC_2H_3(R')$ is constituted by a mixture of radicals:

$$-OCH-CH_2- \text{ and } -O-CH_2-CH-$$
$$\phantom{xxxxx}|\phantom{xxxxxxxxxxxxxxx}|$$
$$\phantom{xxxxx}R'\phantom{xxxxxxxxxxxxxxx}R'$$

and $\overline{n}$ has a statistical average value equal to 2.7 as determined by NMR$^1$H at 500 Hz and R'

| is a mixture of $C_{14}H_{23}$ and $C_{16}H_{33}$ radicals | 1.61 g |
|---|---|
| Cholesterol | 0.40 g |

The procedures given for the first stage in Example 1 are followed.

Second stage:

The lipidic film produced at the end of the first stage is removed and placed in a 60 ml flask. To the lipids 2.03 g of water are added. The resulting mixture is submitted to the following cycle, repeated twice: homogenization using a spatula—oven heating at 75° C. for one hour—return to ambient temperature by spontaneous cooling in air.

Third stage:

The procedure given for the third stage in Example 1 are followed, except that there are employed 14.90 g of a solution containing 1.00% of 5,6-dihydroxyindole and 0.42% of potassium iodide in water.

Fourth stage:

To the dispersion obtained at the end of the third stage, there is added, under mild stirring, 0.20 g of a 0.1M solution of sodium hydroxide in water. The pH of the dispersion is equal to 7.55.

Fifth stage:

The procedures given for the fifth stage of Example 1 are followed, except that there is added 0.90 g of a solution of hydrogen peroxide at 19.1 volumes in water.

The weight composition of the preparation thus produced is the following:

| Nonionic lipid of formula IX | 8.04% |
|---|---|
| Cholesterol | 2.01% |
| Polymerized 5,6-dihydroxyindole | 0.74% |
| Aqueous excipient, sufficient amount for | 100% |

The average size of the dispersed particles (vesicles and pigments), measured after 1 day of storage at ambient temperature, is equal to 285±4 nm; and the average size of the pigments, measured after 8 days of storage at ambient temperature, is equal to 193±2 nm.

EXAMPLE 6

First stage:

A lipidic phase formulated as follows is employed:

| Hydrogenated lecithin, sold by Quest International under the trade name "LECINOL S10" | 2.15 g |
|---|---|
| Cholesterol | 0.57 g |
| Sodium dihexadecylphosphate | 0.14 g |

The aforementioned lipidic components are introduced into a 100 ml round bottom flask and then dissolved at 50° C. in 20 ml of chloroform and 5 ml of methanol. The solvents are then evaporated at 40° C. under reduced pressure, by successive stages, from ambient pressure up to about 500 Pa, using a rotary evaporator.

Second stage:

The procedures given for the second stage of Example 1 are followed, except that 2.89 g of water are used.

Third stage:

The procedures given for the third stage of Example 1 are followed, except that there are employed 20.85 g of a solution containing 1.00% of 5,6-dihydroxyindole and 0.42% of potassium iodide in water.

Fourth stage:

To the dispersion obtained at the end of the third stage, there are added, under mild stirring, 1.50 g of a 0.1M solution of sodium hydroxide in water. The pH of the dispersion is equal to 7.60.

Fifth stage:

The procedures given for the fifth stage of Example 1 are followed, except that 1.26 g of a solution of hydrogen peroxide at 19.1 volumes in water are employed.

The weight composition of the preparation thus produced is the following:

| Hydrogenated lecithin ("LECINOL S10") | 7.32% |
|---|---|
| Cholesterol | 1.95% |
| Sodium dihexadecylphosphate | 0.49% |
| Polymerized 5,6-dihydroxyindole | 0.71% |
| Aqueous excipient, sufficient amount for | 100% |

The volume fraction of the particles dispersed in this preparation (vesicles and pigments based on polymerized 5,6-dihydroxyindole) is equal to 59% after 10 days of storage at ambient temperature.

The average size of the dispersed particles (vesicles and pigments), measured after 10 days of storage at ambient temperature is equal to 379±11 nm; and the average size of the pigments, measured after 21 days of storage at ambient temperature is equal to 291±4 nm.

EXAMPLE 7

First stage:

A lipidic phase formulated as follows is employed:

| Nonionic lipid of formula VIII | 0.58 g |
|---|---|
| Polyoxyethylenated hexadecyl alcohol (20 units of ethylene oxide (EO) on average), sold by ICI ATLAS, under the trade name "BRIJ 58" | 0.55 g |
| Cholesterol | 1.13 g |
| Sodium dihexadecylphosphate | 0.12 g |

The procedures given for the first stage of Example 1 are followed.

Second stage:

The procedures given for the second stage of Example 1 are followed, except that 2.37 g of water are used.

Third stage:

To the lamellar phase obtained at the end of the second stage, there are added 18.95 g of a solution containing 1.00% of 5,6-dihydroxyindole and 0.2% of potassium iodide in water. The mixture thus obtained is stirred by shaking for 15 minutes at ambient temperature and then heated to 30° C. The mixture is then treated for 8 minutes with an ultrasound homogenizer.

Fourth stage:

To the vesicle dispersion obtained at the end of the third step, there is added 0.95 g of a solution of 20 volume hydrogen peroxide in water, and the whole is stirred by shaking for 15 minutes at ambient temperature.

The weight composition of the preparation thus produced is the following:

| Nonionic lipid of formula VIII | 2.43% |
|---|---|
| Polyoxyethylenated hexadecyl alcohol | 2.33% |
| Cholesterol | 4.75% |
| Sodium dihexadecylphosphate | 0.50% |
| Polymerized 5,6-dihydroxyindole | 0.80% |
| Aqueous excipient, sufficient amount for | 100% |

The average size of the dispersed particles (vesicles and pigments), measured after 1 month of storage at ambient temperature is equal to 307±6 nm; and the average size of the pigments, measured after 1 month of storage at ambient temperature, is equal to 122±1 nm.

EXAMPLE 8

A lipidic phase formulated as follows is employed:

| Nonionic lipid of formula VIII | 1.66 g |
|---|---|
| Cholesterol | 1.66 g |
| Sodium dihexadecylphosphate | 0.17 g |

There are introduced into a 100 ml round bottom flask, the aforementioned lipidic constituents which are then dissolved in 15 ml of dichloromethane. The solvent is then evaporated at 40° C. under reduced pressure, by successive stages, from ambient pressure up to about 400 Pa using a rotary evaporator.

17

Second stage:

The lipidic film formed at the end of the first stage is removed and placed in a 60 ml flask. There are added to the lipids 3.53 g of a water/95° ethanol mixture, in the respective amounts of 75/25. The resulting mixture is submitted to the following cycle, repeated twice: homogenization using a spatula—oven heating at 75° C. for 1 hour—return to ambient temperature by spontaneous cooling in air.

Third stage:

The procedures given for the third stage of Example 1 are followed, except that there are added 22.20 g of a solution containing 1.21% of 5,6-dihydroxyindole and 0.51% of potassium iodide in a 75/25 mixture of water/(95°) ethanol.

Fourth stage:

The procedures given for the fourth stage of Example 1 are followed, except that there is added 0.50 g of a 0.1M solution of sodium hydroxide in water. The pH of the dispersion is equal to 8.50.

Fifth stage:

The procedures given for the fifth stage of Example 1 are followed, except that 1.60 g of a solution of 19.9 volumes hydrogen peroxide in water are added.

The weight composition of the preparation thus produced is the following:

| Nonionic lipid of formula VIII | 5.44% |
| --- | --- |
| Cholesterol | 5.44% |
| Sodium dihexadecylphosphate | 0.56% |
| Polymerized 5,6-dihydroxyindole | 0.98% |
| Ethanol | 19.40% |
| Aqueous excipient, sufficient amount for | 100% |

The volume fraction of the particles dispersed in this preparation (vesicles and pigments based on polymerized 5,6-dihydroxyindole) is equal to 41% after 1 day of storage at ambient temperature.

The average size of the pigments, measured after 1 day of storage at ambient temperature, is equal to 295±6 nm.

EXAMPLE 9

First stage:

A lipidic phase formulated as follows is employed:

| Lecithin, sold by Lucas Meyer under the trade name "EPIKURON 200" | 3.04 g |
| --- | --- |
| Cholesterol | 0.76 g |

The procedure given for the first stage of Example 1 is followed.

Second stage:

The lipidic film formed at the end of the first stage is removed and placed in a 60 ml flask. To the lipids are added 3.80 g of water. The resulting mixture is submitted once to the following cycle: homogenization using a spatula—oven heating at 75° C. for 1 hour—return to ambient temperature by spontaneous cooling in air.

Third stage:

To the lamellar phase obtained at the end of the second stage, there are added 23.58 g of a 0.05M solution of silver nitrate in water. The resulting mixture is stirred by shaking for 30 minutes at ambient temperature. The mixture is heated to 30° C. and then treated for 8 minutes using an ultrasound homogenizer.

18

Fourth stage:

To the dispersion of vesicles obtained at the end of the third stage, there are added 1.30 g of a 1M solution of sodium hydroxide in water at a rate of 0.1 ml every 30 seconds. At the end of the addition of the aforementioned sodium hydroxide solution, the pH of the dispersion is close to 11. The dispersion is left to rest at ambient temperature.

The weight composition of the dispersion thus produced is the following:

| Lecithin | 9.36% |
| --- | --- |
| Cholesterol | 2.33% |
| Silver oxide ($Ag_2O$) | 0.42% |
| Aqueous excipient, sufficient amount for | 100% |

The average size of the dispersed particles (vesicles and silver oxide pigments), measured after 1 day of storage at ambient temperature, is equal to 190±3 nm; and the average size of the silver oxide pigments, measured after 1 day of storage at ambient temperature, is equal to 133±1 nm.

EXAMPLE 10

First stage:

A lipidic phase formulated as follows is employed:

| Nonionic lipid of formula VIII | 1.43 g |
| --- | --- |
| Cholesterol | 1.43 g |
| Sodium dihexadecylphosphate | 0.15 g |

The aforementioned constituents are introduced into a 100 ml round bottom flask and then dissolved in 5 ml of dichloromethane. Finally, the solvent is evaporated at 40° C. under reduced pressure, by successive stages, from ambient pressure up to about 400 Pa using a rotary evaporator.

Second stage:

The lipidic film thus formed is removed at the end of the first stage, and placed in a 15 ml flask. To the lipids 3.02 g of water are added. The resulting mixture is submitted to the following cycle which is repeated 6 times: homogenization using a spatula—oven heating at 75° C. for 30 minutes—return to ambient temperature by spontaneous cooling in air.

Third stage:

To the lamellar phase obtained at the end of the second stage, there are added 17.14 g of a solution containing 1.73% of 5,6-dihydroxyindoline hydrobromide in water. The mixture thus obtained is stirred by shaking, for 15 minutes, at ambient temperature.

Fourth stage:

To the dispersion obtained at the end of the third stage, there are added, under mild stirring, 1.3 ml of a 1M solution of sodium hydroxide in water. The pH of the dispersion is equal to 7.50.

Fifth stage:

To the dispersion obtained at the end of the fourth stage, there are added 1.45 g of a solution of 20 volumes hydrogen peroxide in water and then 5.21 g of water. The mixture is treated for 9 minutes with an ultrasound homogenizer.

Sixth stage:

The dispersion is then heated for 4 hours at 80° C. under mild stirring and then left to rest at ambient temperature.

The average size of the dispersed particles (vesicles and pigments), measured after 1 day of storage at ambient temperature, is equal to 1140±160 nm; and the average size of the pigments, measured after 1 day of storage at ambient temperature, is equal to 250±6 nm.

EXAMPLE 11

First stage:

A lipidic phase formulated as follows is employed:

| | |
|---|---|
| Nonionic lipid of formula VIII | 0.72 g |
| Polyoxyethylenated hexadecyl alcohol (20 units of EO on average), sold under the trade name "BRIJ 58" by ICI Atlas | 0.72 g |
| Cholesterol | 1.45 g |
| Sodium dihexadecylphosphate | 0.15 g |

The aforementioned constituents are introduced into a 100 ml round bottom flask and then dissolved in 6 ml of dichloromethane. Finally, the solvent is evaporated at 40° C. under reduced pressure, by successive stages, from ambient pressure up to about 400 Pa, using a rotary evaporator.

Second stage:

The lipidic film formed at the end of the first stage is removed, and placed in a 30 ml flask. To the lipids 3.05 g of water are added. The resulting mixture is submitted to the following cycle which is repeated 4 times:. homogenization with a spatula—oven heating at 75° C. for 30 minutes—return to ambient temperature by spontaneous cooling in air.

Third stage:

To the lamellar phase obtained at the end of the second stage, there are added 17.3 g of a solution containing 0.30 g of indoline hydrobromide and 17 g of water.

The mixture thus obtained is stirred for 15 minutes at ambient temperature using a helix agitator.

Fourth stage:

The dispersion obtained at the end of the third stage is treated for 6 minutes using an ultrasound homogenizer.

Fifth stage:

The pH of the dispersion is adjusted to 11.8 by the addition of 1.3 ml of a 1M solution of sodium hydroxide in water.

1.45 g of a solution of 20 volumes hydrogen peroxide in water are added and then 3.85 g of water, under mild stirring.

Sixth stage:

The resulting dispersion is treated for 2 minutes using an ultrasound homogenizer.

Seventh stage:

The dispersion is stirred using a shaker having oscillating arms for 2 hours at a temperature of 80° C. and then left to rest at ambient temperature.

The average size of the dispersed particles (vesicles and pigments), measured after 1 day of storage at ambient temperature is equal to 294±2 nm; and the average size of the pigments, measured after 1 day of storage at ambient temperature, is equal to 235±40 nm.

We claim:

1. A process for preparing submicronic particles in the presence of lipidic vesicles comprising (a) preparing a dispersion of lipidic vesicles from (i) at least one lipid capable of forming vesicles, (ii) an aqueous phase to be encapsulated in said vesicles, and (iii) an aqueous phase forming a dispersion medium in which said vesicles are dispersed, (b) dissolving at least one polymerizable monomer as a precursor of said submicronic particles in (i') said aqueous phase to be encapsulated in said vesicles, or (ii') in said aqueous phase forming said dispersion medium for said vesicles, or (iii') both (i') and (ii'), and said polymerizable monomer precursor being dissolved in (i'), (ii') or (iii'), at a time (1) before the preparation of a vesicular phase, or
   (2) during the preparation of a vesicular phase, or
   (3) after the preparation of a vesicular phase, or
   (4) both times (1) and (2) or both times (2) and (3), and (c) adding to said polymerizable monomer as a precursor at a time (1) or (2) or (3) or (4), defined above, a polymerization agent capable of transforming said polymerizable monomer precursor into said submicronic particles so as to react with said polymerizable monomer precursor thereby forming said submicronic particles at the exterior of said vesicles or at both the interior and exterior of said vesicles.

2. The process of claim 1 wherein said polymerization agent is added to said polymerizable monomer at a time after the preparation of said vesicular phase.

3. The process of claim 1 wherein said submicronic particles are a polymer and wherein said polymerizable monomer precursor is at least one indolic compound or an indolinic compound or a mixture thereof and said polymerization agent is an oxidation agent or an enzymatic polymerization agent.

4. The process of claim 3 wherein said indolic compound has the formula

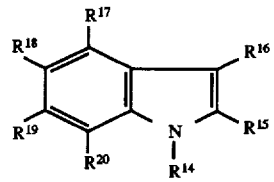

(VI)

wherein $R^{14}$ and $R^{16}$, each independently, represent hydrogen or $C_1$–$C_4$ alkyl;

$R^{15}$ represents hydrogen, $C_1$–$C_4$ alkyl, carboxyl or $C_1$–$C_4$ alkoxy carbonyl;

$R^{17}$ and $R^{20}$, each independently, represent hydrogen, hydroxyl, $C_1$–$C_4$ alkyl, amino, $C_1$–$C_4$ alkoxy, $C_1$–$C_4$ alkoxyoxy or $C_2$–$C_4$ acylamino;

$R^{18}$ represents hydrogen, hydroxy, $C_1$–$C_4$ alkoxy, $C_1$–$C_4$ alkyl, halogen, amino, $C_2$–$C_4$ acyloxy, $C_2$–$C_4$ acylamino or trimethylsilyloxy;

$R^{19}$ represents hydrogen, hydroxy, $C_1$–$C_4$ alkoxy, amino, $C_2$–$C_4$ acyloxy, $C_2$–$C_4$ acylamino, trimethylsilyloxy, $C_2$–$C_4$ hydroxyalkyl amino;

$R^{18}$ and $R^{19}$ being able also to form, together with the carbon atoms to which they are attached, a methylenedioxy ring, optionally substituted by a $C_1$–$C_4$ alkyl group or a $C_1$–$C_4$ alkoxy group, or even a carbonyldioxy ring;

with the proviso that at least one of the $R^{17}$ to $R^{20}$ radicals represents an OZ or $NHR^{21}$ group with at most one of the $R^{17}$ to $R^{20}$ groups representing $NHR^{21}$; and at most two of the $R^{17}$ to $R^{20}$ groups representing OZ and, in the case where Z represents hydrogen, the two OH groups are in positions 5 and 6; and at least one of the $R^{17}$ to $R^{20}$ radicals represents hydrogen, and in the case wherein only one of these radicals represents hydrogen, a single radical among $R^{17}$ to $R^{20}$ then represents $NHR^{21}$ or OZ, the other radicals representing a $C_1$–$C_4$ alkyl; $R^{21}$ representing hydrogen, $C_2$–$C_4$ acyl, $C_2$–$C_4$ hydroxyalkyl, and Z representing hydrogen, $C_2$–$C_{14}$ acyl, $C_1$–$C_4$ alkyl or trimethylsilyl;

or at least one of an alkali metal, alkaline earth metal, ammonium or amine salt thereof, or the hydrochloride, hydrobromide, sulfate or methane sulfonate thereof.

5. The process of claim 4 wherein said indolic compound is selected from the group consisting of 4-hydroxyindole,
5-hydroxyindole,
6-hydroxyindole,
7-hydroxyindole,
4-hydroxy-5-methoxyindole,
4-hydroxy-5-ethoxyindole,
2-carboxy-5-hydroxyindole,
5-hydroxy-6-methoxyindole,
6-hydroxy-7-methoxyindole,
5-methoxy-6-hydroxyindole,
5,6-dihydroxyindole,
N-methyl-5,6-dihydroxyindole,
2-methyl-5,6-dihydroxyindole,
3-methyl-5,6-dihydroxyindole,
2,3-dimethyl-5,6-dihydroxyindole,
2-carboxyl-5,6-dihydroxyindole,
4-hydroxy-5-methylindole,
2-carboxyl-6-hydroxyindole,
6-hydroxy-N-methylindole,
2-ethoxycarbonyl-5,6-dihydroxyindole,
4-hydroxy-7-methoxy-2,3-dimethylindole,
4-hydroxy-5-ethoxy-N-methylindole,
6-hydroxy-5-methoxy-2-methylindole,
6-hydroxy-5-methoxy-2,3-dimethylindole,
6-hydroxy-2-ethoxycarbonylindole,
7-hydroxy-3-methylindole,
5-hydroxy-6-methoxy-2,3-dimethylindole,
5-hydroxy-3-methylindole,
5-acetoxy-6-hydroxyindole,
5-hydroxy-2-ethoxycarbonylindole,
6-hydroxy-2-carboxyl-5-methylindole,
6-hydroxy-2-ethoxycarbonyl-5-methoxyindole,
6-N-β-hydroxyethylaminoindole,
4-aminoindole,
5-aminoindole,
6-aminoindole,
7-aminoindole,
N-methyl-6-β-hydroxyethylaminoindole,
6-amino-2,3-dimethylindole,
6-amino-2,3,4,5-tetramethylindole,
6-amino 2,3,4-trimethylindole,
6-amino-2,3,5-trimethylindole,
6-amino-2,3,6-trimethylindole,
5,6-diacetoxyindole,
5-methoxy-6-acetoxyindole and
5,6-dimethylindole, and the addition salts of these compounds.

6. The process of claim 3 wherein said indolinic compound has the formula

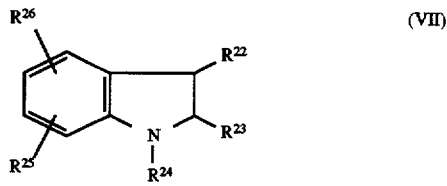

(VII)

wherein $R^{22}$ and $R^{24}$, each independently, represent hydrogen or $C_1$–$C_4$ alkyl, $R^{23}$ represents hydrogen, $C_1$–$C_4$ alkyl, carboxyl or $C_1$–$C_4$ alkoxycarbonyl;

$R^{25}$ represents hydrogen, $C_1$–$C_4$ alkyl, hydroxyl, $C_1$–$C_4$ alkoxy, amino, $C_1$–$C_{10}$ alkylamino or halogen;

$R^{26}$ represents hydrogen, hydroxy, $C_1$–$C_4$ alkoxy or amino; with the proviso that at least one of $R^{25}$ or $R^{26}$ represents hydroxyl, alkoxy or amino; and with the proviso that when $R^{26}$ represents amino, $R^{25}$ cannot represent alkylamino;

$R^{25}$ and $R^{26}$ being also able to form a $C_1$–$C_2$ alkylenedioxy ring when they are in positions 5 and 6; and/or at least one of their alkali metal, alkaline earth metal, ammonium or amine salts, and their hydrochlorides, hydrobromides, sulfates and methane sulfonates.

7. The process of claim 6 wherein said indolinic compound is selected from the group consisting of 5,6-dihydroxyindoline,
6-hydroxyindoline,
5,6-methylenedioxyindoline,
7-methoxy-6-hydroxyindoline,
6,7-dihydroxyindoline,
5-hydroxy-4-methoxyindoline,
4,5-dihydroxyindoline,
5-methoxy-6-hydroxyindoline,
4-hydroxy-5-methoxyindoline,
5-hydroxy-6-methoxyindoline,
4,7-dihydroxyindoline,
6-aminoindoline,
N-ethyl-4-hydroxyindoline,
1-ethyl-6-aminoindoline,
5,6-diaminoindoline,
1-methyl-6-aminoindoline,
2-methyl-6-aminoindoline,
3-methyl-6-aminoindoline,
2-methyl-5,6-diaminoindoline,
5-chloro-7-aminoindoline,
3-methyl-5,7-diaminoindoline,
5,7-diaminoindoline,
2-methyl-5,7-diaminoindoline,
7-aminoindoline,
2-methyl-7-aminoindoline,
4-aminoindoline,
4-amino-6-chloroindoline,
4-amino-6-iodoindoline,
4-amino-5-bromoindoline,
4-amino-5-hydroxyindoline,
4-amino-7-hydroxyindoline,

23

4-amino-5-methoxyindoline,
4-amino-7-methoxyindoline,
5-aminoindoline,
2,3-dimethyl-5-aminoindoline,
1-methyl-5-aminoindoline,
2-methyl-5-aminoindoline,
5-N-(1-methylhexyl) aminoindoline,
5,6-dimethoxyindoline and
5,6-dihydroxy-2-carboxyindoline.

8. The process of claim 1 wherein said submicronic particles are a polymer selected from the group consisting of an acrylamide and a bisacrylamide.

9. A process for preparing submicronic particles in the presence of lipidic vesicles comprising
(a) preparing a dispersion of lipidic vesicles from (i) at least one nonionic amphiphilic lipid capable of forming vesicles, (ii) an aqueous phase to be encapsulated in said vesicles, and (iii) an aqueous phase forming a dispersion medium in which said vesicles are dispersed,
(b) dissolving at least one precursor of said submicronic particles in
(i') said aqueous phase to be encapsulated in said vesicles, or in
(ii') said aqueous phase forming said dispersion medium for said vesicles, or in
(iii') both (i') and (ii'),
said precursor being at least one indolic compound or at least one indolinic compound or a mixture thereof,
said precursor being dissolved in (i'), or (ii') or (iii'), at a time
(1) before the preparation of a vesicular phase, or
(2) during the preparation of a vesicular phase, or
(3) after the preparation of a vesicular phase, or
(4) both times (1) and (2) or both times (2) and (3), and
(c) adding to said precursor at a time (1) or (2) or (3) or (4), defined above, an agent capable of transforming said precursor into said submicronic particles so as to react with said precursor thereby forming said submicronic particles at the exterior of said vesicles or at both the interior and exterior of said vesicles.

10. The process of claim 9 wherein said nonionic amphiphilic lipid is a linear or branched polyglycerol derivative having the formula:

$$R^0O\!-\!\!\left[\,C_3H_5(OH)O\,\right]_{\overline{n}}\!\!-\!H \qquad (I)$$

wherein
—$C_3H_5(OH)O$— is represented by the following structures taken in admixture or separately:

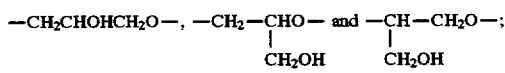

$\overline{n}$ has a statistical average value between 1 and 6;
$R^0$ represents:
(a) a linear or branched, saturated or unsaturated aliphatic chain, containing from 12 to 30 carbon atoms; or

24 hydrocarbon radicals of lanolin alcohol; or the residue of long chain $\alpha$-diols;
(b) the residue $R^1CO$, wherein $R^1$ is a linear or branched aliphatic radical containing $C_{11}$–$C_{29}$ carbon atoms; or
(c) a residue $R^2\!-\![OC_2H_3(R^3)]_{\overline{n}}$ wherein $R^2$ has the meaning (a) or (b) given for $R^0$ and $OC_2H_3(R_3)$ is represented by the following structures, taken in admixture or separately:

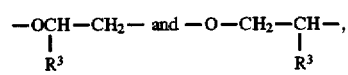

wherein $R^3$ has the meaning (a) given for $R^0$.

11. The process of claim 10 wherein said nonionic amphiphilic lipid has the formula $$C_{16}H_{33}O\!-\!\!\left[\,C_3H_5(OH)O\,\right]_{\overline{n}}\!\!-\!H \qquad (VIII)$$

wherein
—$C_3H_5(OH)O$— is represented by the following structures taken in admixture or separately:

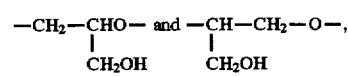

and
$\overline{n}$ has a statistical average value equal to 3.

12. A process for preparing submicronic particles of a metallic sulfide pigment in the presence of lipidic vesicles comprising
(a) preparing a dispersion of lipidic vesicles from (i) at least one lipid capable of forming vesicles, (ii) an aqueous phase to be encapsulated in said vehicles, and (iii) an aqueous phase forming a dispersion medium in which said vesicles are dispersed,
(b) dissolving at least one metallic sulfide pigment in
(i') said aqueous phase to be encapsulated in said vesicles, or
(ii') in said aqueous phase forming said dispersion medium for said vesicles, or
(iii') both (i') and (ii'), and said at least one metallic sulfide pigment being dissolved in (i'), (ii') or (iii'), at a time
(1) before the preparation of a vesicular phase, or
(2) during the preparation of a vesicular phase, or
(3) after the preparation of a vesicular phase, or
(4) both times (1) and (2) or both times (2) and (3), and
(c) adding to said at least one metallic sulfide pigment at a time (1) or (2) or (3) or (4), define above, a precipitation agent capable of transforming said at least one metallic sulfide pigment into said submicronic particles thereby forming said submicronic particles at the exterior of said vesicles or at both the interior and exterior of said vesicles.

13. The process of claim 12, wherein said metallic sulfide pigment is selected from the group consisting of cadmium sulfide, zinc sulfide, lead sulfide and copper sulfide.

* * * * *